United States Patent [19]

Naipawer et al.

[11] 4,052,341

[45] Oct. 4, 1977

[54] 3-METHYL-5-(2,2,3-TRIMETHYLCYCLO-PENT-3-EN-1-YL)PENTAN-2-OL COMPOUND AND PERFUME COMPOSITIONS

[75] Inventors: Richard E. Naipawer, Wallington; William M. Easter, Hasbrouck Heights, both of N.J.

[73] Assignee: Givaudan Corporation, Clifton, N.J.

[21] Appl. No.: 681,351

[22] Filed: Apr. 29, 1976

[51] Int. Cl.$^2$ .............................................. C11B 9/00
[52] U.S. Cl. ............................ 252/522; 260/348.23; 260/586 C; 260/586 R; 260/598; 260/617 C
[58] Field of Search ..................... 252/522; 260/617 C

[56] References Cited

U.S. PATENT DOCUMENTS 3,937,723  2/1976  Schulte-Elte ..................... 252/522

FOREIGN PATENT DOCUMENTS 68,936  9/1969  Germany ............................ 252/522

Primary Examiner—Veronica O'Keefe
Attorney, Agent, or Firm—Thomas Cifelli, Jr.; Robert F. Tavares

[57] ABSTRACT

3-Methyl-5-(2,2,3-trimethylcyclopent-3-en-1-yl)pentan-2-ol possesses a strong, precious woody odor reminiscent of sandalwood oil and is especially valuable in fragrance compositions.

17 Claims, No Drawings

3-METHYL-5-(2,2,3-TRIMETHYLCYCLOPENT-3-EN-1-YL)PENTAN-2-OL COMPOUND AND PERFUME COMPOSITIONS

According to Guenther (E. Guenther, "The Essential Oils", Vol. V, page 173, D. Van Nostrand Co., Inc., New York (1952), East Indian sandalwood oil "has been perhaps one of the most precious perfumery materials from antiquity down to modern times, and its popularity has shown no signs of waning." This oil is widely used in perfumery, and would be even more widely used except for its limited supply and high cost.

As is well known, a need exists for synthetic substances which can be used as sandalwood substitutes or extenders. It would be most desirable to be able to synthetically provide the major odorant compounds of the natural sandalwood oil, i.e. alpha-santalol and beta-santalol, but no commercially feasible route to these chemicals is known at this time.

It would be even more desirable to provide a synthetic compound which would have many of the desirable odor qualities of a fine East Indian sandalwood oil, yet not have the potentially labile primary allylic alcohol group present in the natural santalols. A compound which would be more resistant to acidic or oxidative decomposition as well as being base stable could be even more versatile than sandalwood oil itself.

In accordance with the present invention there is provided novel compositions comprising 3-methyl-5-(2,2,3-trimethylcyclopent-3-en-1-yl)pentan-2-ol which are characterized by a tenacious fine, soft, precious, woody odor reminiscent of sandalwood oil and the naturally occurring santalols.

This invention also provides an economic and commercially feasible process from readily available and low cost starting materials. The process, starting from α-pinene, readily available from turpentine, is illustrated in Chart I.

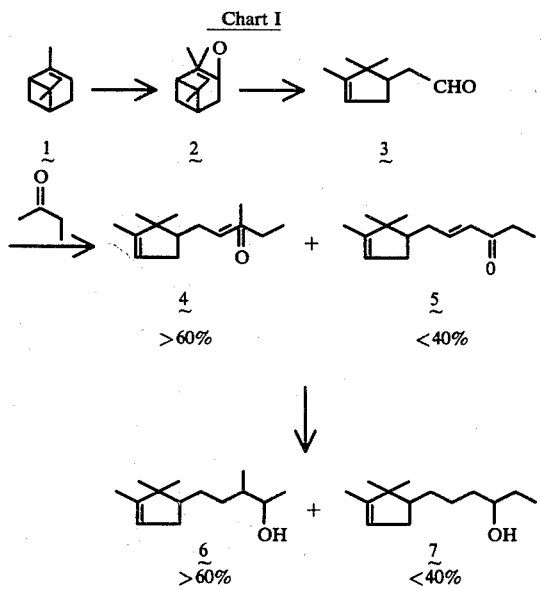

This process involves an epoxidation of α-pinene (1), a rearrangement of the epoxide (2) to campholenic aldehyde (3), a condensation of 3 with 2-butanone and a hydrogenation of the condensation products. Such a process provides a mixture due to the two possible modes by which the condensation step can take place.

Only the 3-methyl-5-(2,2,3-trimethylcyclopent-3-en-1-yl)pentan-2-ol isomer (6) has an intense sandalwood-like odor. The other isomer, 6-(2,2,3-trimethylcyclopent-3-en-1-yl)hexan-3-ol (7) has, surprisingly, a much weaker odor intensity and while it has some woody character, the predominant note is musk-like. The intensity of the minor isomer (7) is so much less than that of the major (6) that its presence does not provide a materially detrimental effect on the odor of 6 until the minor isomer approaches 50%. Indeed, many perfumers expressed a preference for the mixture of 6 and 7 over the pure isomer 6 claiming that the musky note of 7 enhances the odor providing a desirable note of musk while not detracting in any way from the precious wood notes of 6. The musky note, according to these perfumers, makes the composition even more reminiscent of natural sandalwood oil and provides an additional residual sweetness to the odor. This is, of course, fortuitous since the method utilizing the condensation with 2-butanone provides, at the moment, the most economical approach to the desired 3-methyl-5-(2,2,3-trimethylcyclopent-3-en-1-yl)pentan-2-ol (6).

In preparing the compounds of this invention it is preferred, as mentioned previously, to start with the inexpensive and readily available α-pinene. It is well known that α-pinene, a naturally occurring constituent of turpentine, can be obtained as an optically pure substance (both optical antipodes are available), or as mixtures in which both antipodes are present in varying degrees. It has been determined that while the employment of one antipode as starting material leads to a product having an asymmetric center of opposite configuration to the product produced when the other antipode is used, there is no detectable difference in odor of the diasteriomers. Thus, when we speak of 3-methyl-5-(2,2,3-trimethylcyclopent-3-en-1-yl)pentan-2-ol we refer to 3-methyl-5-(2,2,3-trimethylcyclopent-3-en-1(R)-yl)pentan-2-ol or 3methyl-5-(2,2,3-trimethylcyclopent-3-en-1(S)-yl)pentan-2-ol, or mixtures thereof, as equivalents. Each of these products is disclosed in the examples which reveal more fully the properties and preparation of each particular species.

In the preferred synthesis, which is disclosed more fully in the examples, the α-pinene used is converted to the corresponding α-pinene epoxide by means of a peracid epoxidation. The α-pinene epoxide formed is then rearranged into the corresponding campholenic aldehyde, 2-(2,2,3-trimethylcyclopent-3-en-1-yl)acetaldehyde, in the presence of a catalytic amount of a Lewis acid, preferably zinc chloride or zinc bromide and the like.

The campholenic aldehyde so produced can then be converted to the desired novel 3-methyl-5-(2,2,3-trimethylcyclopent-3-en-1-yl)pentan-2-ol and the novel homologs, isomers and analogs described herein in a variety of ways. Chart II illustrates two major pathways by which the compositions disclosed herein can be prepared. Pathway (a) involves the aforementioned condensation with a ketone followed by reduction of the condensation product. In this process, isomeric ketones may result in isomeric mixtures as illustrated in Chart I.

Chart II

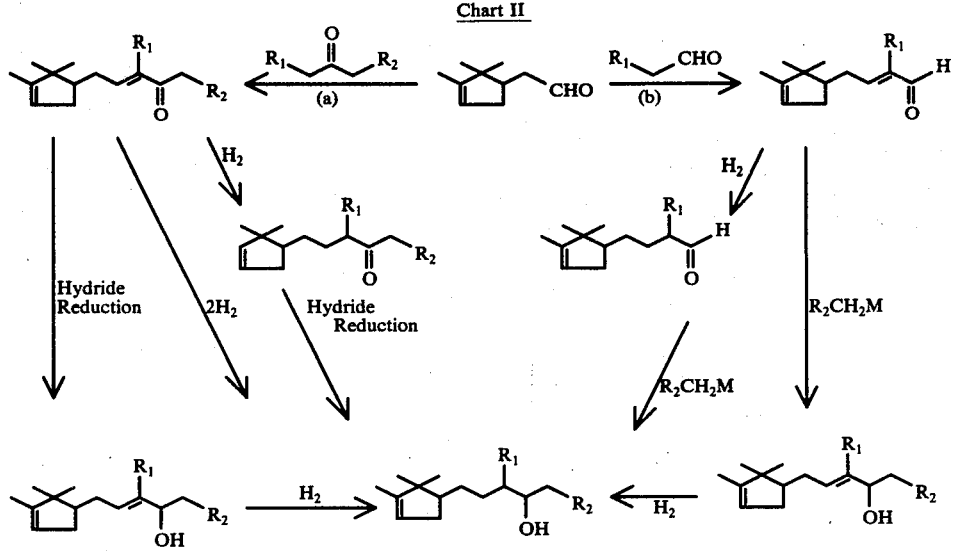

a) $R_1$ = H, $CH_3$, $C_2H_5$
   $R_2$ = H, $CH_3$

Pathway (b) involves a condensation reaction between campholenic aldehyde and an aliphatic aldehyde followed by appropriate hydrogenation and reaction of the carbonyl with an appropriate organometallic reagent to form a secondary alcohol. Pathway (b) allows the preparation of the pure isomers obtained in process (a) when unsymmetrical ketones are used. General variations of these basic pathways are known, some of which are illustrated in greater detail in connection with the examples.

Upon comparison, the novel homologs, isomers and analogs disclosed in this invention, while showing only slight structural differences, show marked differences in odor intensity and quality. Table I shows the structures of the compounds compared.

Table I

| Name* | Structure | Representation |
|---|---|---|
| 3-Methyl-5-(2,2,3-trimethylcyclopent-3-en-1-yl)pentan-2-ol | 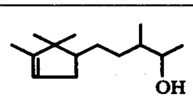 | (6) |
| 3-Methyl-5-(2,2,3-trimethylcyclopentan-1-yl)pentan-2-ol | 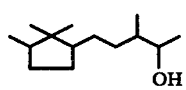 | 8 |
| 5-(2,2,3-Trimethylcyclopent-3-en-1-yl)pentan-2-ol | | 9 |
| 6-(2,2,3-Trimethylcyclopent-3-en-1-yl)hexan-3-ol | | (7)* |
| 4-Methyl-6-(2,2,3-trimethylcyclopent-3-en-1-yl)hexan-3-ol | | 10 |
| 3-Ethyl-5-(2,2,3-trimethylcyclopent-3-en-1-yl)pentan-2-ol | 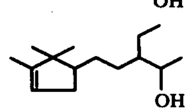 | 11 |
| 3-Methyl-5-(2,2,3-trimethylcyclopent-3-en-1(R)-yl)pentan-2-ol | 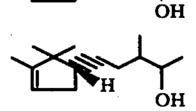 | 6r |
| 3-Methyl-5-(2,2,3-trimethylcyclopent-3-en-1(S)-yl)pentan-2-ol | 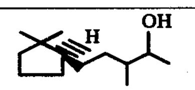 | 6s |
| 3-Methyl-5-(2,2,3-trimethylcyclopent-3-en-1-yl)pent-3-en-2-ol | 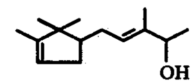 | 12 |

*Names use numbering system to be consistant with one another rather than adhere to preferred conventions.

The characteristic of the 3-methyl-5-(2,2,3-trimethylcyclopent-3-en-1-yl)pentan-2-ol (6) which makes it most useful in perfumery is its intense sandalwood odor. Efforts to find other valuable sandalwood chemicals among the closely related analogs, isomers and homologs were surprisingly unsuccessful. While some of the other compounds had interesting odors, they were much too weak to generate perfumer interest.

For example, if the double bond of 6 is hydrogenated to provide the 3-methyl-5-(2,2,3-trimethylcyclopentan-1-yl)pentan-2-ol (8), the odor is practically eliminated altogether. The odor is very weak, slightly woody and the sandalwood note was described as faint.

Of all the compounds listed in Table I other than 6 and 12, compound 11, the 3-ethyl-5-(2,2,3-trimethylcyclopent-3-en-1-yl)pentan-2-ol, was found to be the strongest in odor intensity. Yet, the intensity of this compound was much too weak to generate perfumer interest. A direct comparison with diluted samples of 6 showed the odor intensity of 11 to be about one-tenth the intensity of 6. Since 8, 9 and 10 are clearly weaker than 11, compound 6 is clearly at least 10 times more intense than any of these others.

Compound 9, a lower homolog, and compound 10, a higher homolog, were both weaker in intensity than 11. In addition to mere intensity differences, the sandalwood character of these compounds was very weak. Compound 9 had less desirable cedar notes, and 10 was more on the musk side than 6. The compound 7, 6-(2,2,3-trimethylcyclopent-3-en-1-yl)hexan-3-ol, was discussed earlier. It too has a very weak odor and has only faint sandalwood notes, its odor being more of the musk-type. The intensity of the odor is so weak that though it is different from the compound 6, it does not detract from the odor of 6 even when substantial amounts are present.

The compounds 6r and 6s are similar in odor to 6 which, as aforementioned, shows that the absolute configuration at the carbon in question has no effect on the odor.

The compound 12 is the only analog of 6 which approaches it in intensity and odor quality. This would imply that the presence or absence of the $\Delta^{3,4}$ olefinic bond has far less influence on the odor properties than do the other subtle changes noted in compounds 7 through 11 wherein the odor characteristics, particularly the intensities, are dramatically changed.

There is no obvious explanation why only slight chemical changes should have such a dramatic effect on odor intensity other than to invoke the general unreliability of odor structure relationships. Why the addition or removal of a methyl group, the removal of a double bond or the mere moving of a methyl group would essentially destroy more than 90% of the odor intensity rather than merely cause subtle odor differences comparable to the subtle chemical differences cannot be explained by any theoretical concepts in the known art.

The comparative compounds (7, 8, 9, 10 and 11) do have some quality notes, but have odors so weak that they have little, if any, value to the perfumer since their effect is lost when diluted in the blending necessary to make perfumes. The desired compounds such as 6, 6r, 6s and 12 have, in contrast, surprisingly strong odors which retain their integrety and hold their own when diluted in perfume blends.

A further advantage is the aforementioned superior stability of the 3-methyl-5-(2,2,3-trimethylcyclopent-3-en-1-yl)pentan-2-ol (6) as opposed to primary allylic alcohols such as sandalwood oil. Compound 6 has been shown in studies to be more stable to heat, oxidizing media and acidic media than the known sandalwood odorants having a primary allylic alcohol group such as the santalols in sandalwood oil.

When the 3-methyl-5-(2,2,3-trimethylcyclopent-3-en-1-yl)pentan-2-ol (6) was incorporated in a soap bar and kept at 140° C for one month, the odor was still judged to be good.

Compound 6 when exposed to sodium hypochlorite solution (household bleach) for 24 hours did not noticeably oxidize. Extraction of the compound from the bleach resulted in a high recovery (no losses due to decomposition etc.) of 6 which remained relatively unchanged. No oxidation occurred. There was no carbonyl absorptions in the ir. When sandalwood oil was subjected to the same conditions, there was material loss (upon extraction) and evidence of substantial oxidation (carbonyl bonds in the ir).

More importantly, while the 3-methyl-5-(2,2,3-trimethylcyclopent-3-en-1-yl)pentan-2-ol (6) retained its fine precious sandalwood odor, the natural sandalwood lost essentially all of its precious sandalwood note and retained only common (cheaper) notes described as piney, woody and fir balsam.

Similarly, when compound 6 was incorporated into a acidic toilet bowl cleaner (pH ~ 1) for one month (32 days) the sandalwood odor remained strong. At the end of the period the oil, extracted from the cleaner, still had a rich, woody, sandalwood-type odor.

In contrast, the odor of natural sandalwood oil was dramatically altered in an identical experiment run at the same time. (Odor differences in the sandalwood oil were noted as early as four days into the experiment). At the end of the experiment (32 days) the fine precious sandalwood character was essentially destroyed and the remaining odor was of the common (cheaper) dry, woody, cedarwood type.

The fact is that the novel compound 6 of this invention is especially valuable because of its remarkable stability and is in many instances superior to the natural sandalwood oil, especially in those cases where the natural material would be susceptible to decomposition. (Note that references to the novel compound 6 includes the optically active compounds 6r and 6s, mixtures of 6r and 6s and the material made via a condensation with 2-butanone which is a mixture of 6 and 7. For the purposes of this invention all are considered to be equivalent with respect to stability and odor utility).

The odor properties of the 3-methyl-5-(2,2,3-trimethylcyclopent-3-en-1-yl)pentan-2-ol (6) are reminiscent of sandalwood oil and the composition can be used in most of the ways sandalwood oil is used. It finds use as a common blender and fixative in a variety of perfume types. There is no particular top note and its odor remains uniform for a considerable length of time. Even on drying out on a perfumer's blotter, the odor remains uniform.

The unusual odor intensity (stronger than sandalwood oil at comparable dilution) allows the perfumer to use smaller amounts and still maintain the desired impact. (The utility in fragrances is treated with more detail in the examples.)

ILLUSTRATION OF PREFERRED EMBODIMENTS

A number of examples are provided herein to illustrate the preferred methods of synthesis of the compounds of this invention and their isomers, homologs and analogs. Among the methods used to characterize the compositions were the following:

1. Infrared spectra (ir) were recorded as neat samples on a Perkin-Elmer Model 457 and absorptions are reported in inverse centimeters.
2. Nuclear magnetic resonance spectra (nmr) were recorded as solutions in chloroform-d$_1$ on a Varian A60A spectrometer and are reported as $\delta$ units relative to tetramethylsilane (TMS) (0.0 $\delta$).
3. Molecular weights were determined on a Perkin-Elmer Model 270 mass spectrometer.
4. Gas-liquid chromatography (glc) was carried out on a 20% Carbowax 20M (6 ft. × ¼ inch) column and/or a 20% SE 30 (6 ft. × ¼ inch column).
5. Unless otherwise indicated weights are in grams, temperatures are in degrees centigrade, pressures are in mm Hg and yields are based on theory.

There is also provided a number of examples illustrating fragrance use, stability and odor intensity.

The examples provided herein are intended only to illustrate the preferred embodiments of this invention and should not be construed as limiting. They are intended to embrace any equivalents or obvious extensions which are known or should be known to a person skilled in the art.

SYNTHESIS

This subsection shows by example and illustration how the compounds of this invention and their homologs can be prepared.

EXAMPLE I

Preparation of Campholenic Aldehyde (3) from α-Pinene (1)

The compounds of this invention, their homologs and other analogs are all available from campholenic aldehyde.

A method used, which is suitably illustrative, involved adding, over a period of 1.5 hours, 420 g (2.2 mol) of 40% peracetic acid to a rapidly stirred suspension of 272 g (2.0 mol) of α-pinene and 307 g (2.9 mol) of sodium carbonate in 400 ml of toluene. During the addition the reaction temperature was maintained at 35°–40° C by means of a cooling bath. The resultant suspension was stirred at 35°–40° C for 35–45 minutes and was quenched by the rapid addition of 1000 ml of water.

The quenched mixture was transferred to a separatory funnel. The lower aqueous layer was then drawn off and re-extracted with 300 ml of toluene. The combined toluene layers were washed once with 400 ml of brine, twice with 400 ml of saturated sodium thiosulfate solution and once again with 300 ml of brine. The solvent was removed by distillation at 75°–85° C (90–100 mm Hg).

The remaining oil was distilled at reduced pressure (15 mm) to yield 17.6 g of recovered α-pinene and 240.8 g (84.7% theory) of the desired α-pinene epoxide (2) (bp 75°–76° C at 15 mm). The product had a molecular weight of 152 (ms), no vinyl hydrogens (nmr) and no absorptions in the ir corresponding to hydroxyl, carbonyl or vinyl hydrogen.

The α-pinene epoxide so produced was then converted to campholenic aldehyde as follows:

To a rapidly stirred refluxing suspension of 7.5 g (0.055 mole) of zinc chloride (anhydrous) in 1000 ml of benzene there was added 304 g (2.0 moles) of α-pinene epoxide over 1.0–1.25 hour period. The resultant mixture was heated at reflux (86° C) for 1.0–1.5 hours, cooled to 25° C and then poured into 400 ml of 5% sodium carbonate solution. The aqueous layer was drawn off and the benzene layer washed twice with 400 ml of brine. The solvent was removed and the oil fractionally distilled to give campholenic aldehyde: 193.2 g (70.2% yield), bp 51°–52° C (1.5 mm); $n_D^{20}$ 1.4658; mol wt. 152 (ms); nmr, 0.8δ (3H, s), 1.0 (3H, s), 1.6 (3H, broad s, olefinic CH$_3$), 2.1–2.6 (4H, broad complex), 5.2 (1H, broad multiplet, olefinic H), 9.7 (1H, doublet of doublets, J~3.5 + 1.5 Hz, aldehyde H); ir, 3020, 2700, 1714, 790 cm$^{-1}$.

Other methods known in the art for epoxidation of olefins may be used. Peracids such as m-chloroperbenzoic acid, trifluoroperacetic acid and the like may also be used for the epoxidation.

The rearrangement of the α-pinene epoxide may also be effected by other Lewis acids, however zinc chloride, zinc bromide and equivalents thereof are preferred.

All commercial grades of α-pinene employed were satisfactory. The presence of the expected impurities such as β-pinene in such commercial grades did not noticeably affect the quality of the final product.

The optical purity of the α-pinene used does not affect the final product of this invention. No noticeable differences in odor were found when odorant compounds of this invention were prepared by starting with either optical antipode of α-pinene ($\alpha_D$ = +40°0' or $\alpha_D$ = −40°0') or a racemic mixture of the two optical isomers.

The campholenic aldehydes, derived from the two optically pure α-pinene samples, were submitted for ORD analysis and the two samples were shown to be mirror images of each other. Both ORD curves cross zero near the sodium-D line, so that both enantiomers exhibit $\alpha_D \sim 0°$. (However, at other wavelengths there is demonstrated measurable rotation as shown by the ORD).

EXAMPLE II

Preparation of α,β Unsaturated Ketones via a Condensation Reaction between Campholenic Aldehyde with Ketones.

Scheme III (below) illustrates a general method used to prepare compounds of the general formula shown below.

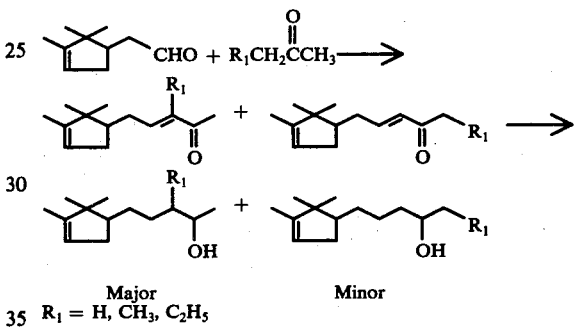

Major    Minor $R_1$ = H, CH$_3$, C$_2$H$_5$

The following examples provide illustrations of the above scheme. First, the preparation of α,β-unsaturated ketones by campholenic aldehyde condensation with ketones is described.

1. Preparation of 3-Methyl-5-(2,2,3-trimethylcyclopent-3-en-1-yl)pent-3-en-2-one (4) from Campholenic Aldehyde and 2-Butanone (methyl ethyl ketone)

This example illustrates a preparation of the above named intermediate by condensing the campholenic aldehyde with methyl ethyl ketone.

To a stirred solution of 400 g (6.1 moles) of methyl ethyl ketone, 1025 g (32 moles) of methanol, 30.5 g (0.54 mole) of potassium hydroxide and 380 g of water cooled to −5° to −10° C was added 152 g (1.0 mole) of campholenic aldehyde over 15–30 minutes. The mixture was maintained at 0° to −10° C for 24–36 hours and then at 25°–35° C for 18–24 hours. The mixture was neutralized by addition of 36.8 g of 62.5% sulfuric acid and the unreacted methyl ethyl ketone and excess methanol were removed by atmospheric distillation. The residual liquid was added to 200 ml of hexane and 200 ml of water. The aqueous layer was drawn off and the hexane layer was washed with 200 ml of brine. The hexane was removed by atmospheric distillation and the oil fractionally distilled under vacuum to give 3-methyl-5-(2,2,3-trimethylcyclopent-3-en-1-yl) pent-3-en-2-one and two other isomers in a ratio of ca. 86:6:8 by glc. Yield 140.3 g (85% theory); bp 102°–105° C (1.3 mm); $n_D^{20}$ 1.4888; mol wt. 206 (ms); nmr, 0.8δ (3H, s), 1.0 (3H, s), 1.6 (3H, broad s), 1.8 (3H, broad s), 2.3 (3H, s, acetyl CH$_3$), 5.3 (1H, broad multiplet, olefinic H), 6.7 (1H, complex, β-olefinic H of an α,β-unsaturated carbonyl system); ir, 3030, 1670, 1635, 790 cm$^{-1}$.

The mass spectral analysis indicates that the condensation product is a mixture of the methyl (A) and ethyl ketones (B & C). In A the condensation took place at the methylene of 2-butanone and in B and C it took place at the methyl group.

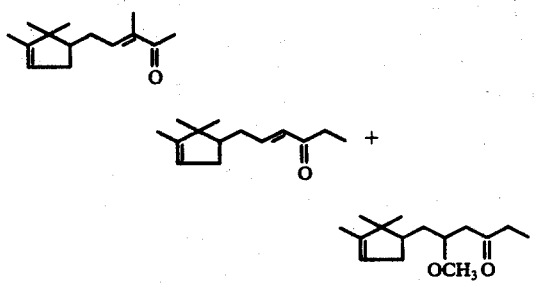

One can vary the conditions of the reaction and alter the isomer ratio. Changes in relative concentrations of reactants and temperature result in variation of reaction time and isomer ratio. The amount of ethyl ketones normally varies between 10% and 30% of the total product, but it does not matter since, upon reduction, the minor alcohol produced (7) has no adverse effect on the odor of the desired product (6).

The obvious modifications can be made. Other hydroxides or alkoxides of alkali metals would be suitable, or any other bases known to be suitable for condensations between aldehydes and ketones. Of course, the readily available sodium or potassium hydroxide are preferred for their economic advantages and ease of handling.

Temperature differences have the expected influence on both the isomer distribution and the reaction rate. (Higher temperatures result in shorter reaction times and slightly lower selectivity. A reaction running at 40° C required about 5 hours.

Other factors such as relative amounts of reactants, concentration etc. are not critical.

2. Preparation of 5-(2,2,3-Trimethylcyclopent-3-en-1-yl)pent-3-en-2-one

The previous example can be repeated substituting an equimolar amount of acetone for ethyl methyl ketone to yield the 5-(2,2,3-trimethylcyclopent-3-en-1-yl) pent-3-en-2-one in good yield. Spectral data were consistent with the structure given.

3. 6-(2,2,3-Trimethylcyclopent-3-en-1-yl)hex-4-en-3-one

The following example shows how the pure ethyl ketone isomer of Example II-1 above (i.e. precursor of isomer 7) can be prepared.

Sodium ethoxide (68 g, 1.0 mol) was slowly added to 1,200 ml ethanol which was being rapidly stirred. A mixture of campholenic aldehyde (152 g, 1.0 mol) and ethyl 2-methylacetoacetate (144 g, 1.0 mol) was added at 25°-30° C over a 35 minute period. The reaction mixture was poured into 2 liters of ice water and the pH adjusted to 2 by adding 25% sulfuric acid. The solid that precipitated was filtered, washed with cold water and dried to yield 68.8 grams of product. The spectral data was consistent with the expected 2-carboxy-5-hydroxy-6-(2,2,3-trimethylcyclopent-3-en-1-yl)hexan-3-one in the enol form.

The 68.8 grams of solid was charged with 550 ml ethanol, 400 ml water and 10 g of 62.5% sulfuric acid into a 2-liter flask connected to a gas meter. The reaction mixture was heated at reflux for 24 hours during which time the solid slowly dissolved and carbon dioxide was evolved. After pouring into water, extracting with ether, removing the solvent and distilling, the resulting oil provided a working sample of 6-(2,2,3-trimethylcyclopent-3-en-1-yl)hex-4-en-3-one which proved to be identical to the minor isomer obtained when 2- butanone was reacted with campholenic aldehyde.

EXAMPLE III

Selective Hydrogenation of the α,β-Unsaturated Ketones to Provide the Desired Secondary Alcohols The following examples illustrate a method for completely hydrogenating the alkyl portion of molecule while leaving the double bond of the ring intact.

1. Preparation of 3-Methyl-5-(2,2,3-trimethylcyclopent-3-en-1-yl)pentan-2-ol (6)

Into a one-liter stainless steel autoclave was charged 350 g (1.7 moles) of 3-methyl-5-(2,2,3-trimethylcyclopent-3-en-1-yl)pent-3-en-2-one, 26.3 g (7.5 wgt-%) of copper chromite, 0.1 g (0.03 wgt-%) of potassium hydroxide and 250 ml of sec.-butyl alcohol. The mixture was stirred and heated to 160° C under 300 psi hydrogen pressure and was hydrogenated until the hydrogen uptake ceased. The mixture was cooled to ambient temperature. The autoclave was vented and then the reaction mixture removed and filtered through a thin pad of Filter-cel ®. The solvent was removed from the filtrate by distillation to a pot temperature of 75° C at 10-15 mm. The residual viscous oil was fractionally distilled to give 3-methyl-5-(2,2,3-trimethylcyclopent-3-en-1-yl)pentan-2-ol (a mixture of diastereomers). Yield 310 g (87% theory); bp 103°-106° C (1.0 mm); n$_D^{20}$ 1.4730; mol wt. 210 (ms); nmr, 0.5δ, 0.8, 0.9 and 1.0 (6H, 4s, geminal dimethyl groups of the various diastereomers in the mixture), 1.0-1.1 (3H, d, buried under the CH$_3$ singlets), 1.12 and 1.15 (3H, 2d, J=6.5 Hz, carbinol methyl groups of the various diastereomers in the mixture), 1.2-1.5 (6H, broad complex), 1.6 (3H, broad s, olefinic CH$_3$), 1.7 (1H, s, hydroxyl H/exchanged by D$_2$O, 1.8-2.4 (2H, broad complex, allylic methylene), 3.7 (1H, broad multiplet, carbinyl H), 5.2 (1H, broad multiplet, olefinic H); ir, 3360, 3040, 790 cm$^{-1}$.

2. 6-(2,2,3-Trimethylcyclopent-3-en-1-yl)hexan-3-ol (7)

This example provides an alternate method for selectively reducing the α,β-unsaturated ketones to saturated alcohols without at the same time reducing the olefinic bond in the cyclopentyl ring.

Lithium wire (2.21 g, 316 mgm-atoms) was added to 250 ml of freshly distilled ammonia. A solution of 6-(2,2,3-trimethylcyclopent-3-en-1-yl)hex-4-en-3-one (12.6 g, 61.9 mmoles) in 60 ml of dimethoxyethane (DME) was added slowly (30 minutes). The mixture was stirred at reflux for 1.0 hour. Excess lithium was then destroyed by slow, cautious addition of solid NH$_4$Cl until the blue color disappeared. The ammonia was then evaporated and 50 ml DME was added.

The product was isolated and distilled to provide the desired 6-(2,2,3-trimethylcyclopent-3-en-1-yl) hexan-3-one. Spectral analysis showed the ring double bond to be intact while the α,β-unsaturation had been reduced.

The ketone was then subjected to a sodium borohydride reduction to provide 6-(2,2,3-trimethylcyclopent-3-en-1-yl)hexan-3-ol which proved to be identical to the minor isomer (7).

EXAMPLE IV

Preparation of α,β-Unsaturated Aldehydes via a Condensation Reaction between Campholenic Aldehyde and Aliphatic Aldehydes The following scheme illustrates a method used to prepare compounds of the general formula shown below. This route avoids the isomeric mixtures resulting when nonsymmetrical ketones are condensed with campholenic aldehyde.

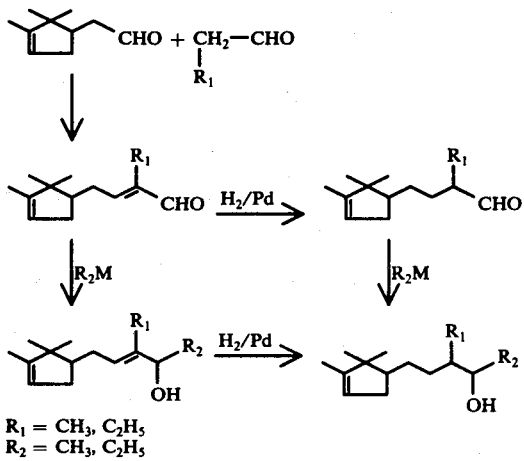

$R_1 = CH_3, C_2H_5$
$R_2 = CH_3, C_2H_5$

The following examples illustrate suitable experimental procedures for condensation reactions between campholenic aldehyde and normal alkyl aldehydes.

1. 2-Methyl-4-(2,2,3-trimethylcyclopent-3-en-1-yl)but-2-enal

A mixture of campholenic aldehyde (456 g, 3.0 mol) and freshly distilled propionaldehyde (348 g, 6.0 mol) was slowly added, over a 1.0 hour period, to a stirred refluxing solution of 18 ml of 40% aqueous sodium hydroxide and 800 ml methanol. The mixture was refluxed an additional two hours, cooled to room temperature and poured into 1,000 ml of water. The resultant solution was extracted three times with 300 ml of hexane. The hexane extracts were combined, washed first with 600 ml of water and then with 600 ml of brine. The solvent was removed by distillation and the oil fractionally distilled to yield the 2-methyl-4-(2,2,3-trimethylcyclopent-3-en-1-yl)but-2-enal. Yield 323 g (56.1% theory); bp 64°-65° C (0.9 mm); mol wt. 192 (ms); ir, 3035, 2710, 1690 (s), 1640 (s), 800 cm⁻¹; nmr, 0.8δ and 1.0 (6H, 2s, geminal dimethyl groups), 1.7 (3H, broad s, olefinic methyl attached to the cyclopentenyl group), 1.9-2.2 (3H, broad multiplet), 2.3-2.6 (3H, broad multiplet), 5.3 (1H, broad multiplet, olefinic H), 6.6 (1H, t, J~7.5 Hz), 9.4 (1H, sharp s, aldehyde H).

2. 2-Ethyl-4-(2,2,3-Trimethylcyclopent-3-en--yl)but-2-enal

Following the procedure under 1 on a one third molar scale and employing n-butyraldehyde in place of propionaldehyde there was obtained 2-ethyl-4-(2,2,3-trimethylcyclopent-3-en-1-yl)but-2enal. Yield 128.3 g (62.3% theory); bp 124°-125° C (1.8 mm); mol wt 206 (ms); ir, 3040, 2710, 1675 (s), 1635 (s), 790 cm⁻¹; nmr, 0.9δ and 1.0 (6H, 2s, geminal dimethyl group), 1.0 (3H, t, methyl of the ethyl group), 1.6 (3H broad s, olefinic methyl), 1.8-2.7 (6H, complex), 5.3 (1H, broad multiplet, olefinic H of the cyclopentenyl ring), 6.4 (1H, t, J~7.5 Hz, olefinic Hβ to the aldehyde group), 9.2 (1H, sharp s, aldehyde H).

In either of the above examples an optically active product can be obtained starting with an optically active campholenic aldehyde. As shown herein, the chirality of the asymmetric center of campholenic aldehyde has no effect on the odor of the final product.

EXAMPLE V

Selective Reduction of the α,β-Unsaturated Double Bond of the α,β-Unsaturated Aldehydes The following procedures illustrate a selective conversion of the α,β-unsaturated aldehyde to a saturated aldehyde while leaving the cyclic double bond intact (see scheme of Example 4).

1. 2-Methyl-4-(2,2,3-trimethylcyclopent-3-en-1-yl)butanal

A mixture of 111 g (0.58 mole) of 2-methyl-4-(2,2,3-trimethylcyclopent-3-en-1-yl)but-2-enal, 2.7 g of 5% palladium on carbon and 80 ml of ethanol was hydrogenated at 30°-40° C and 40-55 psi until hydrogen uptake ceases. The mixture was filtered to remove the catalyst and the solvent removed by distillation. The residual oil was fractionally distilled to yield 2-methyl-4-(2,2,3-trimethylcyclopent-3-en-1-yl)butanal. Yield 110.7 g (98.4% theory); bp 60°-61° (1.4 mm); mol wt. 194 (ms); ir, 3040, 2700, 1728 (s), 800 cm⁻¹; nmr, 0.5δ, 0.8, 0.9 and 1.0 (6H, 4 s, geminal dimethyl groups of various diastereomers in the mixture), 1.1 (3H, d, J~7 Hz), 1.3-2.6 (7H, broad complex), 1.6 (3H broad s, olefinic methyl), 5.2 (1H, broad multiplet, olefinic H), 9.7 (1H, d, J~1.5 Hz, aldehyde H).

2. 2-Ethyl-4-(2,2,3-Trimethylcyclopent-3-en-1-yl)butanal

By a similar procedure there was produced 2-ethyl-4-(2,2,3-trimethylcyclopent-3-en-1-yl)butanal: Yield - 98.2% theory; bp 93°-95° C (1.5 mm); mol wt 208 (ms); ir, 3040, 2700, 1725 (s), 800 cm⁻¹; nmr 0.5δ, 0.8, 0.9 and 1.0 (6H, 4s, geminal dimethyl groups of the various diastereoisomers in the mixture), 0.94 (3H, t, J~6 Hz, methyl of the ethyl group), 1.1-2.5 (10H, broad complex), 1.6 (3H, broad, s, olefinic methyl), 5.2 (1H, broad multiplet, olefinic H), 9.45 and 9.47 (1H, 2d, J~2 Hz, aldehyde H of the diastereoisomeric aldehydes).

EXAMPLE VI

Preparation of Secondary Alcohols from Aldehydes

The following procedures illustrate the reaction of the aldehyde and a suitable organometallic to provide secondary alcohols as shown in the scheme of Example IV.

1.

3-Ethyl-5-(2,2,3-Trimethylcyclopent-3-en-1-yl)pentan-2-ol

To a mixture of 117 ml (0.24 mole) of 2.06 M methyllithium (in ether) cooled to 5° C was added a solution of 39.0 g (0.19 mole) of 2-ethyl-4-(2,2,3-trimethylcyclopent-3-en-1-yl)butanal in 200 ml of anhydrous ether. The addition was carried out at 5°-10° C over 1 hour and the resultant mixture refluxed for 2 hours.

The mixture was cooled to 5° C and 50 ml of saturated sodium sulfate solution was added slowly. The mixture was poured into 300 ml of water. The aqueous layer was drawn off and extracted twice with 100 ml portions of ether. The ether extracts were combined, washed with water and brine, dried over magnesium sulfate and concentrated by removing the solvent. The residual oil was fractionally distilled to yield 3-ethyl-5-(2,2,3-trimethylcyclopent-3-en-1-yl)pentan-2-ol. Yield 30.5 g (71.7% theory); bp 116°-119° C (1.5 mm); mol wt 224 (ms); ir, 3360 (s, broad, 3040, 800 cm$^{-1}$, no absorptions in the 2700-2800 and 1650-1750 cm$^{-1}$ regions; nmr, 0.5δ, 0.8, 0.9 and 1.0 (6H, 4s, geminal dimethyls of the various diastereomers in the mixture), 1.1 (3H, t, J~5.5 Hz, methyl of the ethyl group), 1.2 (3H, d, J~6.5 Hz, carbinol methyl), 1.2-2.5 (11H, broad complex), 1.6 (3H, broad s, olefinic CH$_3$), 3.8 (1H, broad multiplet, carbinyl H), 5.2 (1H, broad multiplet, olefinic H).

2.

4-Methyl-6-(2,2,3-Trimethylcyclopent-3-en-1-yl)hexan-3-ol

Similarly, employing a Grignard reaction with ethylmagnesium iodide there was prepared 4-methyl-6-(2,2,3-trimethylcyclopent-3-en-1-yl)hexan-3-ol. Yield 73.1% theory; bp 95°-97° C (2.0 mm); mol wt 224 (ms); ir, 3360 (s, broad), 3040, 800 cm$^{-1}$, no absorption in the 2700-2800 and 1650-1750 cm$^{-1}$ regions; nmr, 0.8δ and 1.0 (6H, 2s, geminal dimethyls), 0.96 (3H, t, J~6.5 Hz), 0.90 (3H, d, J~5 Hz), 1.2-2.5 (10H, complex), 1.6 (3H, broad s, olefinic methyl), 1.7 (1H, s, exchanged with D$_2$O, hydroxyl), 3.4 (1H, broad multiplet, carbinyl H), 5.2 (1H, broad multiplet, olefinic H).

3.

3-Methyl-5-(2,2,3-Trimethylcyclopent-3-en-1-yl)pentan-2-ol

A solution of 20.8 g (0.12 mole) of 2-methyl-4-(2,2,3-trimethylcyclopent-3-en-1-yl)butanal dissolved in ethyl ether-anhydrous (50 ml) was added to a stirred solution of methyllithium (1.7 M) in ethyl ether (250 ml; 0.14 mole) which was previously cooled to 0° C. The mixture was stirred at 0°-5° C for 1.0 hour and then heated at reflux (36° C) for 3.0 hours. The mixture was cooled to 0° C and excess methyllithium was decomposed by slow dropwise addition of saturated sodium sulfate solution (50 ml). The mixture was poured into 150 ml of water, the lower aqueous layer was drawn off and extracted twice with 100 ml of ether. The ether extracts were combined, washed with 150 ml of brine, dried over sodium sulfate, filtered and the solvent removed by distillation. The residual oil was fractionally distilled to yield 3-methyl-5-(2,2,3-trimethylcyclopent-3-en-1-yl)pentan-2-ol: 20.4 g (81% yield); bp 96°-98° (0.9 mm); mol wt. 210 (ms).

EXAMPLE VII

3-Methyl-5-(2,2,3-Trimethylcyclopentan-1-yl)pentan-2-ol

A mixture of 105 g (0.5 mole) of 3-methyl-5-(2,2,3-trimethylcyclopent-3-en-1-yl)pentan-2-ol, 5.3 g of 5% palladium on carbon and 100 ml of ethanol was hydrogenated at 30°-45° C and 35-50 psi until the hydrogen uptake ceased. The mixture was filtered to remove the catalyst and the solvent was removed from the filtrate by distillation. The residual oil was fractionally distilled to yield 3-methyl-5-(2,2,3-trimethylcyclopentan-1-yl)pentan-2-ol: 93.2 g (97.3% yield); bp 105°-107° C (1.3 mm); mol wt 212 (ms);

ir, 3350 (s, broad) cm$^{-1}$. No absorption in the 3010-3080 cm$^{-1}$ region or the 750-850 cm$^{-1}$ region, indicating no olefinic hydrogens and no trisubstituted olefin, respectively.

nmr, 0.5δ and 0.85 (6H, 2s, geminal dimethyl groups), 0.7-1.0 (6H, broad multiplet), 1.1 (3H, 2d, carbinol methyl groups of various diastereomers in the mixture), 1.3-2.0 (11H, broad complex), 2.2 (1H, broad s, exchanged with D$_2$O, hydroxyl H), 3.65δ (1H, broad multiplet, carbinyl H), no absorptions in the 5.07-7.0δ region indicating no olefinic protons.

EXAMPLE VIII

5-(2,2,3-Trimethylcyclopent-3-en-1-yl)pentan-2-ol

To a stirred solution of 13.3 g (0.35 mole) of sodium borohydride and 0.3 g of sodium hydroxide in 200 ml of ethanol and 20 ml of water was added 86.4 g (0.45 mole) of 5-(2,2,3-trimethylcyclopent-3-en-1-yl)pent-3-2-one at 25°-40° C over 15 minutes. The resultant mixture was stirred at ambient temperature for 18 hours and was then poured in a mixture of 300 ml of water and 30 ml of 10% sodium hydroxide solution. The mixture was extracted with hexane and the combined hexane extracts were washed neutral with several brine washes. The hexane was removed by distillation and the residual oil was fractionally distilled to give a mixture of 5-(2,2,3-trimethylcyclopent-3-en-1-yl)-pent-3-en-2-ol (66%) and 5-(2,2,3-trimethylcyclopent-3-en-1-yl)pentan-2-ol (22%): 57.4 g (65% yield) bp 94°-108° C (1.4 mm); mol wt. 194 and 196 (ms), respectively.

A mixture of 0.6 g of 5% palladium on carbon, 44.1 g (0.15 moles of the pent-3-en-2-ol) of the above pentenol/pentanol mixture and 50 ml of ethanol was hydrogenated at 25°-45° C and 35-52 psi until hydrogen uptake ceased. The mixture was filtered to remove the catalyst and the solvent was removed from the filtrate by distillation. The residual oil was fractionally distilled to yield 5-(2,2,3-trimethylcyclopent-3-en-1-yl)-pentan-2-ol 30.1 g (77.7% yield); bp 105-108° C (1.5 mm); mol wt. 196 (ms); ir, 3350 (s, broad), 3040 and 797 cm$^{-1}$; nmr, 0.5δ, 0.8, 0.9 and 1.0 (6H, 4s, geminal dimethyl groups of various diastereomers in the mixture), 1.2 (3H, d, J~6 H$_z$, carbinol methyl), 1.3-1.5 (7H, broad complex), 1.6 (3H, broad s, olefinic methyl), 1.7-2.4 (3H, broad complex containing 1H exchangeable with D$_2$O), 3.8 (1H, broad multiplet, carbinyl H), 5.2 (1H, broad multiplet, olefinic H).

EXAMPLE IX

Odor Quality and Intensity Comparisons

1. Pure 3-methyl-5-(2,2,3-trimethylcyclopent-3-en-1-yl) pentan-2-ol (6) was compared with compositions of (6) with 25%, 40% and 50% of 6-(2,2,3-trimethylcyclopent-3-en-1-yl) hexan-3-ol, respectively.

At levels of 25% of 7 the mixture was described as closer to natural sandalwood oil due to the musk note which was felt to enhance the final product. It was also agreed that the mixture was less intense then the pure isomer, probably due to dilution.

At levels of 40% of 7, the musk note was slightly more pronounced and the overall intensity was further weakened. However, the composition still had a fine sandalwood odor and, althrough slightly less preferred than the 75:25 mixture, was still considered to be hightly desirable.

At levels of 50% or more of 7 the odor becomes flat and was considered less desirable. However, it was not ruled out that such mixtures would be preferred for certain applications. Again, the odor intensity is diminished and apparently the musk note has reached an awareness level so as to detract from the fine, precious, sandalwood note of the isomer 6.

2. The following tests were run to determine the magnitude by which the odor intensity of compound 6 was greater than the much less intense comparative compounds of Table I. First, to choose the strongest among the weak, three perfumers independently compared coded samples of 7, 8, 9, 10 and 11. Each, independently and without reservation chose the sample containing compound 11 as the most intense.

In a separate test a sample of compound 11, 3-ethyl-5-(2,2,3-trimethylcyclopent-3-en-1-yl)pentan-2-ol was compared to a 75:25 mixture of 6 and 7 [3-methyl-5-(2,2,3-trimethylcyclopent-3-en-1-yl)pentan-2-ol (6) and 6-(2,2,3-trimethylcyclopent-3-en-1-yl) hexane-3-ol (7)]) respectively. Separate solutions of the 75:25 mixture were prepared in diethylphthalate wherein the level of ordorant was 1%, 5%, 10% and 20% by weight respectively. These samples were coded by a party who did not participate in the comparison and who did not reveal the code to the participants.

The participants, 2 quality control perfumers and 1 research perfumer, were asked to match the sample of 11 (undiluted) with the coded sample that they felt matched it most closely in intensity. Independently, two of the participants matched it as weaker than the 10% sample but stronger than the 5% sample. One matched it as stronger than the 1% sample but weaker than the 5% sample.

In no case did the participants know which of the samples were of which concentration so that the grading of the reference samples acted as an internal check on the comprison data.

EXAMPLE X

Stability

The following examples illustrate the stability of the 3-methyl-5-(2,2,3-trimethylcyclopent-3-en-1-yl)-pentan-2-ol (6).

1. Thermal Stability in Soap

A sandalwood composition of this invention (75%-6 + 25%-7) was incorporated at a 1% level in a soap bar which was stored for 1 month at 140° C. At the end of the test period a soap evaluation panel (5 members) judged the odor as still good.

2. Stability in Household Bleach

This example illustrates the stability of a sandalwood composition of this invention (ca. 75%-6 and 25%-7) in oxidizing media such as bleach. The following examples were run in triplicate.

To 200 g of 10% sodium hypochlorite solution (ordinary household bleach) was added in one instance 2.0 grams of 3-methyl-5-(2,2,3-trimethylcyclopent-3-en-1-yl)pentan-2-ol (ca 75%-6 and 25%-7) and in the other instance 2.0 grams of East Indian Sandalwood Oil.

The mixtures were stirred for 24 hours. Ether (50 ml) was added to each of the flasks, the mixture stirred well for 15 minutes, and the layers allowed to separate. The aqueous layer was further extracted 3 times with 50 ml portions of ether. The combined ether layers were washed with saturated (sodium chloride) salt solution and concentrated.

From the natural sandalwood oil there was recovered an average of 1.5 grams. The recovered oil and the starting material were compared. A comparison of the infrared data showed that the —OH band of the processed oil was much weaker in intensity and there were strong carbonyl (C=O) bands which revealed that significant oxidation had taken place. Further evidence for oxidation was obtained by extracting an average of 0.6 grams of acidic materials from the aqueous layer.

Of greater significance was the fact that the sandalwood oil which had been stirred in the bleach had lost its fine, precious, sandalwood notes. The recovered material had only the common (cheaper) notes described as piney, woody and fir balsam indicating the santalols had been destroyed.

In contrast, the average recovery of the sandalwood composition of this invention was greater than 90%. The infrared of the recovered material showed a strong -OH band and very little in the carbonyl region indicating that very little oxidation, if any, had occurred.

Most importantly, the recovered oil still had the fine, precious, sandalwood notes and virtually no odor change. The data clearly indicates the far greater stability of the sandalwood composition of this invention.

3. Stability in low pH Toilet Bowl Cleaner

This example illustrates the stability of the sandalwood composition of this invention, called Compound A below, (ca 75%-6 and 25%-7) in a low pH cleaner. These "acidic" cleaners pose special problems to the perfumer since many odorants are destroyed by the acid.

Two samples of a low pH toilet bowl cleaner, consisting of 9% concentrated hydrochloric acid, 3% emulsifiers, and 88% distilled water, were perfumed with 1% of compound A and East Indian Sandalwood Oil, respectively. The samples were agitated daily and odor evaluated over the course of one month. Throughout the month, the odor of the sample containing Compound A remained stronger and the odor character retained the rich woodiness of Compound A itself. The sample containing East Indian Sandalwood Oil continually changed throughout the month and the precious woody odor changed to a sour, dry, cedarwood-type odor.

After one month, the two samples were extracted with ether, the solvent was removed, and the Compound A and East Indian Sandalwood Oil were respectively evaluated against the starting materials. Although the odor of Compound A had been modified somewhat, the rich, woody sandal-wood-type odor was still present. The extracted Sandalwood Oil had a sour, dry, cedar-type odor and was no longer reminiscent of sandalwood.

ODORANT COMPOSITIONS

The following examples are offered to illustrate the utility of the sandalwood compositions of this invention in a variety of fragrance compositions. In each of the examples, Compound A is one of the compositions of this invention was claimed such as 6 or 6r or 6s or 12 or the mixture of 6 (>60%) and 7 (>40%) as described in Table I and elsewhere in this specification.

EXAMPLE XI

This example illustrates how the novel compositions of this invention can be employed as the basis for a synthetic sandalwood oil.

| Consider the following fragrance formulation: | |
|---|---|
| Compound A | 200 |
| Sandela, ®* 50% in Diethyl-phthalate | 700 |
| α-Methyl ionone | 50 |
| American Cedarwood Oil | 50 |
| | 1,000 |

*Registered Trademark of Givaudan Corporation for a polycyclic alcohol product having a sandalwood odor.

When Compound A is the aforementioned mixture of 6 and 7, 12, 6r or 6s; the addition contributes valuable sandalwood notes providing the resulting composition with a stronger, more rounded body of precious wood character.

When compared to the base composition, wherein Compound A has been replaced by the odorless diethylphthalate, contribution of Compound A becomes apparent. The odor without Compound A is weaker and less reminiscent of the natural sandalwood oil.

Substitution of the comparative compounds (7, 8, 9, 10 or 11) for Compound A in the formula did not perceptibly improve the odor of the base formula. Their odor impact was too weak to make a significant contribution.

EXAMPLE XII

The following example illustrates the utility of the sandalwood compositions of this invention in fragrance compositions of the woody type. Compound A is a novel composition of this invention as previously defined. The effect that the presence, absence or changing of Compound A has on the fragrance follows the example.

| 1. | The Use of Compound A in a Woody-type Composition | |
|---|---|---|
| | Component | pts |
| | Compound A | 280 |
| | Oranger liquid | 20 |
| | Limonene | 38 |
| | Linalool | 66 |
| | Linalyl acetate | 95 |
| | Benzyl acetate | 20 |
| | γ-Methyl ionone | 152 |
| | p-tert.-Butylcyclohexyl acetate | 114 |
| | Vetiver acetate | 115 |
| | Coumarin | 40 |
| | Versalide ®* | 30 |
| | Aldehyde C-12, 10% DPG | 4 |
| | Undecalactone, 10% DPG | 6 |
| | Diphenyl oxide | 10 |
| | Diphenyl methane | 10 |
| | Total | 1,000 |

*Registered trademark of Givaudan Corporation for 1,1,4,4-Tetramethyl-6-ethyl-7-acetyl-1,2,3,4-tetrahydronaphthalene Compound A contributes body to the woody odor making it fuller, deeper, richer and providing an overall rounding effect. The total odor effect of the added Compound A on this composition is reminiscent of the effect achieved when natural sandalwood is used in the same manner.

The dryout odor of the composition containing Compound A is fuller and stronger, especially in the musky notes, and lasts longer than the dryout odor of the base composition without Compound A.

The observation suggests that the novel compositions of this invention have fixative properties similar to those achieved with musks and with natural sandalwood oil.

At concentrations lower than 28% quoted in this example, the effects are similar but less pronounced. Higher concentrations may also be used successfully for unique and special effects.

When Compound A is replaced by one of the comparative compounds (7, 8, 9, 10 or 11) the effect on the base composition (i.e. the composition without Compound A) is very weak and minimal, the odor impact of such comparative compounds being too weak to make a significant contribution.

EXAMPLE XIII

The following example illustrates the utility of the sandalwood compositions of this invention in fragrance compositions of the muguet type. Compound A is a novel composition of this invention as previously defined.

| 2. | The Use of Compound A in a Muguet-type Composition | |
|---|---|---|
| | Component | pts |
| | Compound A | 142 |
| | Aldehyde C-9, n-Nonanal, 10% diethyl phthalate | 2.5 |
| | Aldehyde C-10, n-Decanal, 10% DEP | 1 |
| | Amyl cinnamic aldehyde | 13 |
| | Benzyl acetate | 25 |
| | Benzyl salicylate | 20 |
| | Cinnamyl acetate | 45 |
| | Cyclamen aldehyde, α-methyl-p-isopropyl phenylpropionaldehyde | 10 |
| | Citronellyl acetate | 30 |
| | Phenyl methyl carbinyl acetate, 10% DEP | 45 |
| | Hexyl cinnamic aldehyde | 20 |
| | Indole, 2,3-benzylpyrrole, 10% DEP | 4 |
| | Laurine ®, Hydroxycitronellal | 120 |
| | Linalool, cour | 140 |
| | Linalyl cinnamate | 40 |
| | Nerol, prime | 40 |
| | Phenyl ethyl alcohol | 130 |
| | Phenyl ethyl isobutyrate | 4 |
| | Phenyl ethyl dimethyl carbinol | 10 |
| | Phenyl ethyl phenyl acetate | 25 |
| | Rhodinol, extra | 60 |
| | Rhodinyl acetate | 34 |
| | Terpineol | 50 |
| | Tetrahydrolinalool | 30 |
| | Total | 1,000 |

Compound A imparts to the composition a "naturalness" by contributing to the woody and stem notes thus making the total odor more like the odor of the whole flower in its natural environment. The effect is reminiscent of the contribution made by natural sandalwood oil.

On dryout, the composition containing Compound A has a much stronger and longer lasting odor than the composition without Compound A, an indication once again of the fixative properties of Compound A.

EXAMPLE XIV

Compound A was tested in a number of other "odor type" perfumes at a level of 0.5% to determine what effect it would have on these odor types.

In certain types (Fougere, Chypre, animal complex, classic citrus cologne) the effect was to provide "lift." The top notes were accentuated and the whole odor impression was more brilliant and full.

In florals (Rose, Muguet, Jasmin, Lilac) the odor effect was to provide natural notes, depth and fullness. The fragrance was richer and rounded. For example, the rose composition lost its geranium sharpness and the green notes became more prominent. The whole odor impression was more rounded and pleasing.

Samples on a perfumer's blotter which were examined after 18 hours, 24 hours, and 48 hours, when compared with the compositions without Compound A, were stronger, deeper, and longer lasting, clearly demonstrating the fixative properties of the added compound.

We claim:

1. A composition consisting essentially of from less than 100% to more than 60% of 3-methyl-5-(2,2,3-trimethylcyclopent-3-en-1-yl)pentan-2-ol and a definite amount, but not more than 40%, of 6-(2,2,3-trimethylcyclopent-3-en-1-yl)hexan-3-ol.

2. A composition according to claim 1 wherein the 3-methyl-5-(2,2,3-trimethylcyclopent-3-en-1-yl)pentan-2-ol is between 70% and 90% and the 6-(2,2,3-trimethylcyclopent-3-en-1-yl)hexan-3-ol is between 30% and 10%.

3. A composition according to claim 1 wherein the 3-methyl-5-(2,2,3-trimethylcyclopent-3-en-1-yl)pentan-2-ol is about 75% and the 5-(2,2,3-trimethylcyclopent-3-en-1-yl)hexan-3-ol is about 25%.

4. 3-Methyl-5-(2,2,3-trimethylcyclopent-3-en-1-yl)pentan-2-ol.

5. 3-Methyl-5-(2,2,3-trimethylcyclopent-3-en-1-yl)pent-3-en-2-ol.

6. 3-Methyl-5-(2,2,3-trimethylcyclopent-3-en-1(R)-yl)pentan-2-ol).

7. 3-Methyl-5-(2,2,3-trimethylcyclopent-3-en-1(S)-yl)pentan-2-ol. -(

8. A fragrance composition comprising an olfactorily effective amount of a composition consisting essentially of from less than 100% to more than 60% of 3-methyl-5-(2,2,3-trimethylcyclopent-3-en-1-yl)pentan-2-ol and a definite amount, but not more than 40% of 6-(2,2,3-trimethylcyclopent-3-en-1-yl)hexan-3-ol and at least one other olfactory agent.

9. A fragrance composition according to claim 8 wherein the 3-methyl-5-(2,2,3-trimethylcyclopent-3-en-1-yl)pentan-2-ol is between 70% and 90% and the 6-(2,2,3-trimethylcyclopent-3-en-1-yl)hexan-3-ol is between 30% and 10%.

10. A fragrance composition according to claim 8 wherein the 3-methyl-5-(2,2,3-trimethylcyclopent-3-en-1-yl)pentan-2-ol is about 75% and the 5-(2,2,3-trimethylcyclopent-3-en-1-yl)hexan-3-ol is about 25%.

11. A fragrance composition comprising an olfactorily effective amount of the compound of claim 4 and at least one other olfactory agent.

12. A fragrance composition comprising an olfactorily effective amount of the compound of claim 5 and at least one other olfactory agent.

13. A method for improving the odor of a fragrance composition which comprises adding thereto an effective amount of the composition of claim 1.

14. A method for improving the odor of a fragrance composition which comprises adding thereto an effective amount of the composition of claim 2.

15. A method for improving the odor of a fragrance composition which comprises adding thereto an effective amount of the composition of claim 3.

16. A method for improving the odor of a fragrance composition which comprises adding thereto an effective amount of the composition of claim 4.

17. A method for improving the odor of a fragrance composition which comprises adding thereto an effective amount of the composition of claim 5.

* * * * *